US010660568B2

United States Patent
King

(10) Patent No.: US 10,660,568 B2
(45) Date of Patent: May 26, 2020

(54) SENSOR MODULE FOR MEASURING BODY PARAMETERS

(71) Applicant: Rudolf King, Altenstadt (DE)

(72) Inventor: Rudolf King, Altenstadt (DE)

( * ) Notice: Subject to any disclaimer, the term of this patent is extended or adjusted under 35 U.S.C. 154(b) by 180 days.

(21) Appl. No.: 15/755,557

(22) PCT Filed: Aug. 18, 2016

(86) PCT No.: PCT/EP2016/069612
§ 371 (c)(1),
(2) Date: Feb. 27, 2018

(87) PCT Pub. No.: WO2017/050494
PCT Pub. Date: Mar. 30, 2017

(65) Prior Publication Data
US 2018/0249955 A1    Sep. 6, 2018

(30) Foreign Application Priority Data

Sep. 21, 2015 (DE) .................... 20 2015 006 491 U

(51) Int. Cl.
*A61B 5/00* (2006.01)
*A61B 5/01* (2006.01)
(Continued)

(52) U.S. Cl.
CPC .......... *A61B 5/6801* (2013.01); *A61B 5/0006* (2013.01); *A61B 5/0022* (2013.01);
(Continued)

(58) Field of Classification Search
CPC ... A61B 5/6801; A61B 5/0006; A61B 5/0022; A61B 5/01; A61B 5/021; A61B 5/0402;
(Continued)

(56) References Cited

U.S. PATENT DOCUMENTS

2003/0163287 A1  8/2003  Vock et al.
2005/0080322 A1  4/2005  Korman
(Continued)

FOREIGN PATENT DOCUMENTS

WO    2013134845 A1    9/2013

OTHER PUBLICATIONS

International Search Report of PCT Patent Application No. PCT/EP2016/069612 dated Nov. 14, 2016.

*Primary Examiner* — Paula J Stice

(57) ABSTRACT

The invention relates to a sensor module for body parameters and to a method for transmitting, receiving, and storing information about the behavior of a user during sport, movement, and at rest. Said information is determined from at least one of various biometric sensors, GPS chips, girometers, and others, location, speed, movement and other devices (measuring devices) measuring at least one status or a status change. The information is then transmitted by means of at least one radio chip connected to the measuring device, wherein the measuring devices are not networked with or connected to one another, but the transmission is rather carried out directly from the respective measuring device and radio chip, the measuring module, to one or more servers, preferably by means of mobile internet, mobile telephone data link, or another radio link.

15 Claims, 2 Drawing Sheets

(51) Int. Cl.
  *A61B 5/021* (2006.01)
  *A61B 5/0402* (2006.01)
  *A61B 5/145* (2006.01)
  *G16H 40/67* (2018.01)
  *G16H 10/60* (2018.01)

(52) U.S. Cl.
  CPC ............... *A61B 5/01* (2013.01); *A61B 5/021* (2013.01); *A61B 5/0402* (2013.01); *A61B 5/14532* (2013.01); *G16H 10/60* (2018.01); *G16H 40/67* (2018.01); *A61B 2562/0219* (2013.01)

(58) Field of Classification Search
  CPC ........ A61B 5/14532; A61B 2562/0219; G16H 40/67; G16H 10/60
  See application file for complete search history.

(56) References Cited

U.S. PATENT DOCUMENTS

2010/0315225 A1* 12/2010 Teague ................ A61B 5/0024
                                                          340/539.12
2016/0150958 A1*  6/2016 Kranz .................. A61B 5/0006
                                                          600/515

\* cited by examiner

SENSOR MODULE FOR MEASURING BODY PARAMETERS

FIELD OF THE INVENTION

The present invention concerns a sensor module for body parameters. In particular, it concerns a sensor module for body parameters and a method for the sending, receiving and storing of information about the behaviour of a user during sport, movement and at rest. The said information is determined from at least one of various biometric sensors, GPS chips, girometers and others, location, speed, movement and other devices (measuring devices) which measure at least one status or a change in status. The information is then transmitted by means of a radio chip connected to the measuring device, wherein the measuring devices are not networked with or connected to one another, but rather the transmission is made directly from the respective measuring device and radio chip, the measuring module, to one or a number of servers, preferably by means of mobile internet, telephone data link or another radio link.

STATE OF THE ART

Due to the emergence and the improvement of cheap sensors and the ever further increasing use of mobile phones with computing power, known as smartphones there is a trend towards user self-monitoring, in particular towards evaluation of sports types, especially in athletics, in jogging/running, Nordic walking and also in other types of sports such as in the area of weight training.

This trend has been further fed by the more recent emergence of so-called smartwatches, miniaturisation of watches (sports watches) specifically intended for sports and preferably wearable on the wrist, which can both measure, amongst other things, pulse and other values by means of sensors which are integrated or frequently wirelessly connected via Bluetooth, and which, for example, record routes via a GPS chip. The data collected by them is immediately processed in the smartphone, in the smartwatch or other sports watch and made available to, for example, a runner for self-monitoring. Further, they can be uploaded later via the internet to a server or the cloud and stored there as a type of sports diary, in order to illustrate the user's training achievements.

The most popular sports sensors are pulse monitors which are currently still frequently carried in a chest strap, but also already on the wrist and can also be found incorporated in smartwatches or sports watches. With the combination of GPS chip and pulse monitoring device a runner can see for example the speed range he is currently in, or in retrospect was in, and what his exercising pulse is or was in order to be able adapt his training frequently immediately or in subsequent training areas.

As described, the sensors and other measuring devices, in particular GPS chips girometers are either already incorporated in the specific sports watch; GPS chips are also frequently present in smartphones, as well as girometers and other sensors; pulse monitors, in particular, are frequently still externally attached. The connection is frequently made by a so-called handshake process in which the sensor transmits specific information to the device for storing or processing by the device which is connected via Bluetooth. However, this comes up against some limitations which are sometimes serious.

Current methods of monitoring sports and other aspects of lifestyle and those which have emerged over the last 5 years or so, as described above, have some limitations due to their central structure.

1. Low Energy Density of the Connection From Sensor to Receiving Device

In so far as the connectivity between the sensor and the receiving device—smartphone, smartwatch or sports watch—is lost because of the low energy density caused by the structure, battery and system, the monitoring cannot be carried out albeit that the sensor itself regularly continues to deliver information which, however, cannot be transmitted because of the weak connection.

2. Restricted Computing Power of the Receiving Devices

Because of limited computing power which smartphones have despite the high quality computing chips built in today, complex computing operations cannot be carried out, especially where there are several connected sensors and especially where the detected values must be compared against one another.

3. Multiple Sensor Connections

It is often not technically possible to connect more than one sensor to the receiving device.

4. Applications and Sensors Spanning an Insufficient Range of Sports Types

To the extent that a user participates in various sports types which require different measurements, he frequently needs a number of monitoring devices because of the complexity of the measurements and the associated computing operations.

5. Failings of the Receiving Device

Many of the devices are difficult to carry on the body or are otherwise unwieldy so that ad hoc sports performance is frequently not recorded.

If, for example, a runner passes a park and has his sports kit with him and decides, perhaps on the spur of the moment, to go for a short run he may not have packed the correct sports watch as this was not planned in advance.

If he decides for example to use his smartphone to record the sporting exercise but has not packed the correct carrying bag (the so-called "pouch") for his smartphone, he is presented with the choice of carrying the smartphone in his hand or doing without the recording. Carrying the mobile phone in his hand can be dangerous if he falls or if it slips out of his hand. Furthermore, sweat could run into the mobile phone since it is not protected.

6. Overloading of Receiving Devices With Complex Computing Operations

Smartphones are frequently overloaded by complex computing operations especially when a number of programs are running simultaneously which are not necessarily relevant to sports.

Thus, if the user wants to have GPS positioning switched on at the same time as monitoring his pulse and also listening to music using the MP3 function of the mobile phone, the smartphone can rapidly reach the limits of its capacity and potentially, partially or completely crash.

7. Battery Drainage in the Receiving Device Caused by Receiving and Computing Operations The battery of the receiving device can quickly be drained by complex receive functions and computing operations whereby the training exercise cannot be completely recorded or, in the worst case, data from completed activities may be lost.

8. Lack of Compatibility Between Different Sensors (Lack of Compatibility)

Inter-compatibility between different sensors and manufacturers is often deliberately and intentionally (on the part of industry) restricted or even excluded, in order to protect the independence of the manufacturer. Frequently, two sensors from different manufacturers cannot be connected nor their data transmitted, to the same receiving device, even though the smartphone itself can open a number of Bluetooth or WLAN channels.

9. No Uniform Possibility for Comparison on Different Systems

Finally, there is no uniform platform for comparison so that the user will frequently be unable to combine information on one training exercise captured on a sports watch specific to one type of sport with information determined by another measuring device, which for example is not made by the same manufacturer.

DEFINITIONS

GSM chip: any chip or other electronic device which can establish a connection to a server preferably by means of mobile internet, telephone data link or another radio link in any frequency range—thus also by light, laser or infra-red—and transmissions in other frequencies, frequently via HDSPA/H/G/3G LTE network and also on other radio frequencies reserved for regulatory authorities, emergency services and the military. The designation GSM indicates that the standard application can be carried out by means of normal mobile phone networks.

Module: a combination of a measuring device and a GSM chip which controls and makes the transmission in conjunction with a—preferably re-chargeable—battery. Thus the measuring device xxx, which works together with both the battery and radio chip according to the method, always bears the name xxx module.

Server: a dedicated server or the so-called cloud connected to the module preferably via mobile internet connection or radio link.

GPS: any satellite supported positioning system for telematics, so currently GPS (USA), GLONAS (GUS) and Galileo (Europe), but also terrestrial positioning systems such as via GPRS, GSM positioning and LORAN.

SHORT DESCRIPTION OF THE INVENTION

Figure 1:
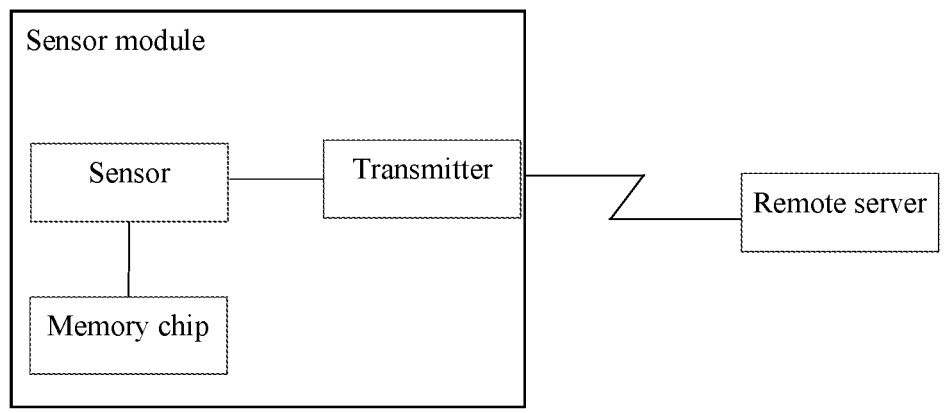
FIG. 1 is a block diagram of a sensor module according to a first embodiment of the present application.
Figure 2:
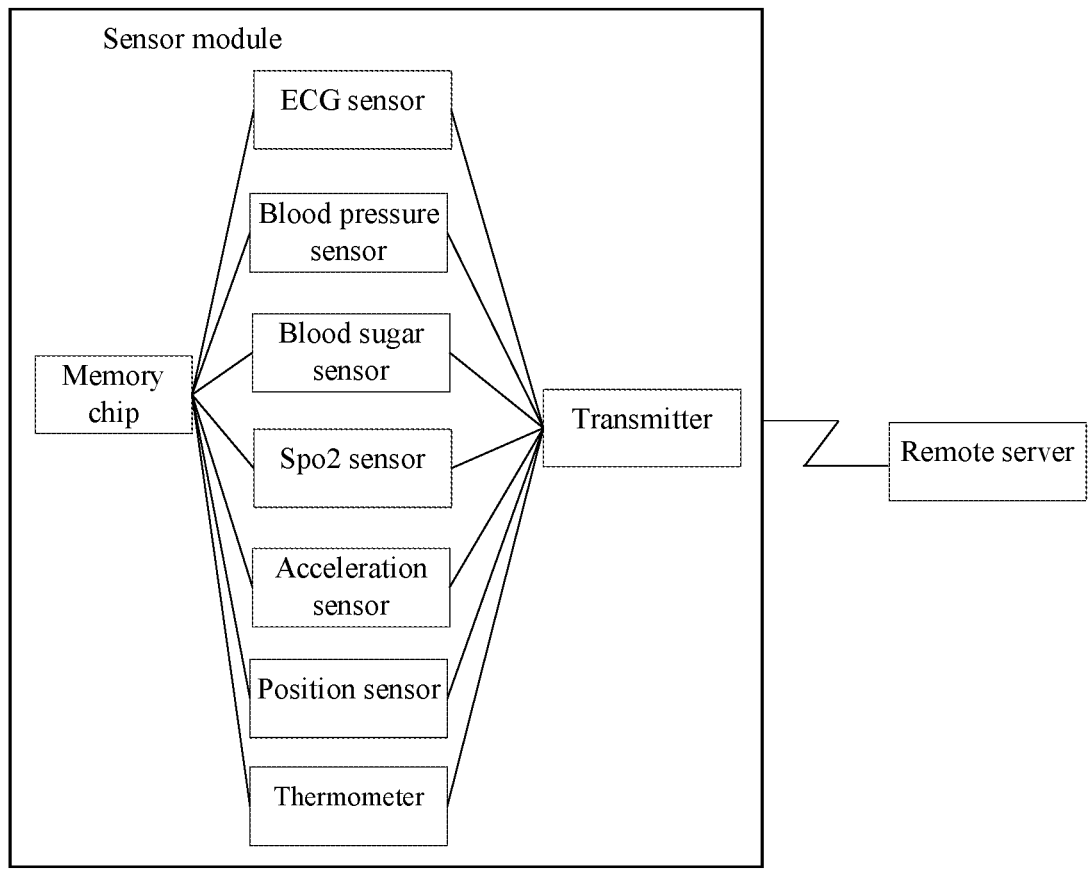
FIG. 2 is a block diagram of a sensor module according to a second embodiment of the present application.
Figure 3:
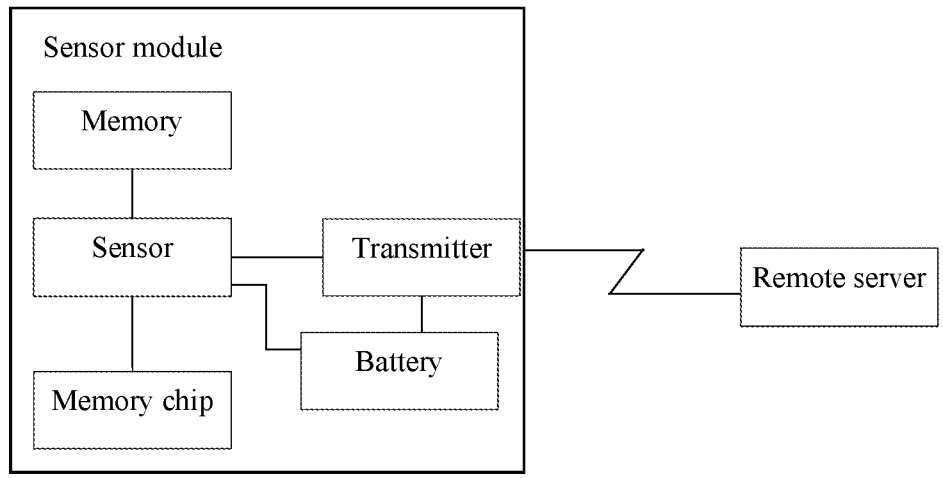
FIG. 3 is a block diagram of a sensor module according to a third embodiment of the present application.
Figure 4:
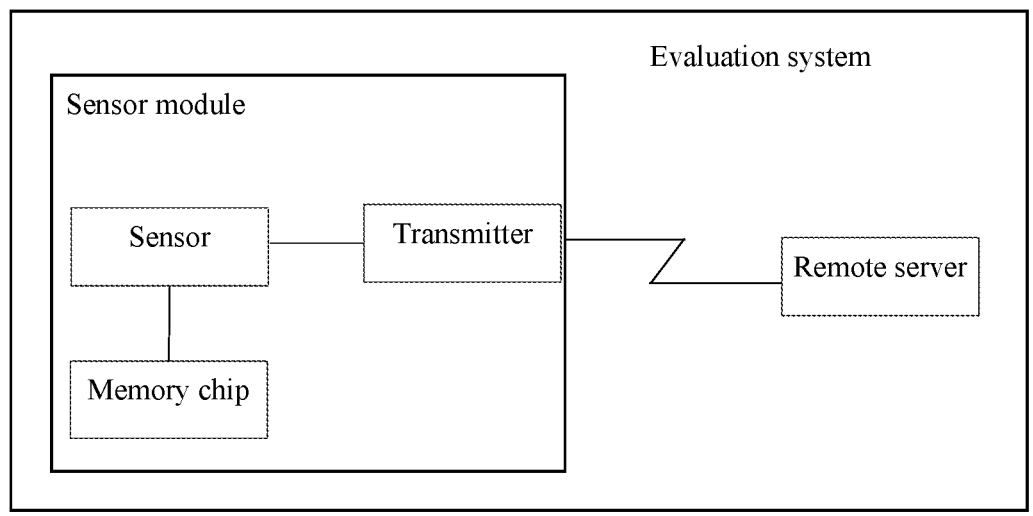
FIG. 4 is a block diagram of an evaluation system according to an embodiment of the present application.

The Referring to FIGS. 1-4, the present invention concerns a sensor module for body parameters. The module is preferably adapted exclusively for sending data to a remote server. In an active state the sensor sends the captured data (preferably symmetrically encrypted) at predetermined intervals, without knowing whether a receiver can utilize the data.

In a preferred embodiment a sensor module for body parameters is provided which is adapted to be carried on the user's body, comprising at least one sensor which measures at least one parameter in order to generate corresponding sensor data, and one transmitter module which is connected and adapted to the sensor, in order to receive the sensor data from the sensor and send it directly to a remote server.

In a preferred embodiment a sensor module is made available which is adapted to be incorporated in a sports device or sports equipment or to be attached to an animal comprising at least one sensor which measures at least one parameter in order to generate corresponding sensor data, and one transmitter module which is connected and adapted to the sensor, in order to receive the sensor data from the sensor and send it directly to a remote server.

In a preferred embodiment the sensor module for body parameters is not capable of receiving and/or processing information from the remote server or any other source.

In a preferred embodiment the transmitter module additionally sends a user identifier of the user to the remote server. This user identifier can either be set by the user, for example by means of suitable software when the module is connected to a PC, or may be inherently specified in the module wherein the identifier can be assigned to the user when the user undergoes a registration process.

In a preferred embodiment the at least one sensor is selected from a group consisting of an ECG sensor, a blood pressure sensor, a blood sugar sensor, an SpO2 sensor, an acceleration sensor, a position sensor and a thermometer.

In a preferred embodiment the transmitter module is adapted to use at least one mobile communications standard in order to transmit the sensor data to the remote server, wherein the mobile communications standard is preferably selected from the group consisting of a public radio network standard, the regional mobile network standard, GSM, GPRS, Edge UMTS, HSDPA, HSPA+, LTE and LTE advanced.

In a preferred embodiment the transmitter module is a one-way transmission system.

In a preferred embodiment the sensor module for body parameters is only designed to transmit information and not to receive queries or instructions.

In a preferred embodiment the transmitter module is adapted to use at least one short-range radio frequency and wherein the short-range radio frequency preferably corresponds to a communications standard selected from the group consisting of Bluetooth, IEEE 802.11 and IEEE 802.11 a, ac, ad, b, g, h or n.

In a preferred embodiment the sensor module for body parameters further comprises a battery which supplies energy to the transmitter module and the sensor and a memory module which is adapted to store the sensor data, preferably in case the battery power has become too weak to supply the transmitter with enough energy. Thus in this embodiment, at least one of the modules detects the fact that the battery can no longer provide sufficient power in order to maintain the transmitter module's functionality, or that the battery is approaching that level of capacity. This can also be detected by an extra processor, or similar, provided in the sensor module for body parameters. The data from the measuring module is subsequently transmitted to the memory unit and stored there. The memory unit is a non-volatile memory.

In a preferred embodiment the measurement data transmitted to the server further comprises a device identifier, personal identifier and/or time identifier for at least one user.

In a preferred embodiment the sensor module for body parameters further comprises a memory chip which is adapted to provide interim storage for the data if there is a short-term failure of radio links and/or power supply and to send the whole of the data when the radio links are restored, or to provide longer-term storage and send it in data packets.

In a preferred embodiment the sensor module is adapted so that where a measuring threshold is exceeded, measurement distance intervals are adjusted to correspond to the exceedance, in order for example to make possible a better positioning and thereby a more accurate distance when making a difficult measurement.

In a preferred embodiment the sensor module for body parameters further comprises an interface for connecting the sensor module for body parameters for subsequent overplaying and evaluation of measurement data.

In a preferred embodiment the sensor module is incorporated in a ball.

In a preferred embodiment the sensor module is incorporated in a club/racket/bat.

In a preferred embodiment the sensor module is incorporated in the sole of a shoe.

In a preferred embodiment the sensor module is incorporated in an ODP module.

The present invention further provides an evaluation system for a sensor module for body parameters which comprises a sensor module according to the above description; and a remote server in which the data from the transmitter module is received, wherein the measurement data of a user transmitted to the server is summarised and/or evaluated in the server within a prescribed time frame.

In a preferred embodiment timing data from different sensors and measuring devices is reconciled on the server by means of synchronisation by sending an identifier to a module and comparing the send-and-return time in order to detect a deviation by the sensor from the actual time.

In a preferred embodiment the remote server is adapted to directly store and/or evaluate the information received from the sensor module for body parameters.

In a preferred embodiment the server sends instructions to a user's mobile device which were determined by means of an algorithm stored on the server from at least one characteristic variable of the sensor module for body parameters.

DETAILED DESCRIPTION OF THE PREFERRED EMBODIMENTS

A method is described for the sending, receiving and storing of information about the behaviour of a user during sport, movement and at rest. The said information is determined from at least one of various biometric sensors, GPS chips, girometers and others, location, speed, movement and other devices (measuring devices) which measure at least one status or a change in status. The information is then transmitted by means of a radio chip connected to the measuring device, wherein the measuring devices are not networked with or connected to one another, but rather the transmission is made directly from the respective measuring device and radio chip, the measuring module, to one or a number of servers, preferably by means of mobile internet, telephone data link or another radio link.

A method is described for reconciling the times of the data received in this way, and a method for subsequent or simultaneous evaluation and further processing of the captured, transmitted and stored data.

A method for changing the status of the sensors, initiated by the server or by an algorithm integrated into the measuring device, a method for returning instructions from the server to a receiving unit for the direct information of the user, preferably by means of headphones or another microphone with a mobile radio link (receiver module), also by means of a smartphone or mobile phone.

Description of various measuring modules; description of a switch module as well as the embedding of measuring modules in the soles of shoes, also with the option of motion charging, in golf, tennis and other rackets and aids used in sport, in balls and other throwing devices, which according to the rules of the sport type, leave the area of the user.

Description of the combination of various switching and measuring modules and the ideal combination of a number of measuring units with just one radio chip as a combination module.

Algorithm for changing the measuring intervals from the server and/or the hardware itself, especially in the case of GPS modules and girometers for recognising the type of sport and movement of the user.

Involvement of "operational data provisioning" (shortened to ODP) modules in motor sport. ODP defines a number of interfaces for data which are classified as motion data or master data (attributes, texts or hierarchies). Once implemented, the interfaces make it possible to access the data for reporting and analysis as well as for the replication of mass data.

Method for connecting existing devices in sports studios ("gyms"), which devices have their own read-out units, to the server of the above-mentioned method directly online, or indirectly by means of card reader modules with a transmission path.

Description of a method of energy saving by Wifi connections, especially in the case of modules preferably used or which can be used in buildings and of a method for using drones in the method described in combination with a GPS module and potentially a switch module.

A) Data Flow

1. Decoupling of the Measuring Devices and Transmission of Values to a Server

Measuring devices are decoupled from a standard receiving device (frequently a smartphone, smartwatch, or sports watch) and the measured values are singly, i.e. without communication and other connections between devices, transmitted to the server by means of the radio link, preferably mobile internet, telephone data link or other radio link in any frequency range—so also via light, laser and infra-red and transmissions in other frequencies. At the server they are immediately stored and then simultaneously or subsequently processed together.

2. Relocation of Computing Functions

In order to make complex computing performance possible, all computing operations, whether simultaneous or subsequent, are relocated from the mobile device to a server.

3. Overall Function

If the measured data as well as the device's identifier are sent from a measuring device to the server singly in the manner described above, including the time of transmission, this data can be directly assigned to at least one user either from the device identifier or by direct transmission of the personal identification number.

Regardless of whether the evaluation now takes place simultaneously or subsequently, the values assigned to a user can be summarised within a specific time frame and from them any type of calculation stored in an algorithm can be carried out.

The information produced in this way can be transmitted back to a receiving device, to be described below, and communicated to the user or one or a number of third parties for immediate application.

Example: If single measurement data such as pulse rate as well as the device identifier is transmitted from a measuring device such as a pulse belt to the server in the manner described, including the time of transmission, this data can be directly assigned to at least one user from the device identifier or by direct transmission of the personal identification number. The same applies for a measured GPS location, whether it is sent out directly or transmitted singly from an application on a smartphone. Further sensors as well as further measuring devices can transmit information in the same way.

Regardless of whether the evaluation is carried out simultaneously or subsequently, the values assigned to a user can be summarised within a specific time frame and from them any type of calculation stored in an algorithm can be carried out.

This information can be forwarded from the server to the user or third parties by a receiving device.

Example: A computing operation according to the described method can be a combining of the GPS data with the pulse data, from which height, distance run, and speed can respectively be presented compared against the pulse data. It can be recorded that a training exercise should performed completely or partially at a particular speed. If too high or too low a heart rate is now detected from transmitted data in which GPS data is compared against pulse, or too high or too low a speed is detected just from the speed calculated from the distance between two recorded GPS locations in one time interval, the information ascertained in this way can be transmitted back to a receiving device (to be described below) and communicated to a user or one or a number of third parties—a trainer, training partner, judges or other persons for immediate application and information, in order to know how a person is progressing in a competition such as a cross-country run or also to send first-aid assistance if dehydration or a fall are detected.

B) Hardware

Alongside the already described:

1. —GPS module (this type of hardware, without the described method, can already be found being applied in electronic leg restraints used in US law enforcement and for the geo-fencing of Alzheimer's patients), 2. —girometer module, and 3. —pulse module, currently conceivable modules are:

4. —SpO2 modules (measurement and transmission of blood-oxygen saturation),

5. —diabetes/CGM (constant glucose monitoring) modules,

6. —modules with any other sensor and measuring device which can measure reasonable values in at least approximate real time, and which values can describe directly or indirectly a status, or a change in a status of a person.

Further described are:

7. —a Bluetooth module,

8. —a WiFi modules,

9. —a switch module, and

10. —a camera module.

11. A module can also be attached to an object or an animal, if this can result in conclusions being drawn about a sporting or other performance.

Example: being built into a car in motor sport, attachment to a horse in order to recognise the behaviour of or also a fall by a horse; GPS modules for hounds and horses in fox-hunting. Combination of two modules with one girometer module on the rider and one girometer module on the horse in order to draw conclusions about the cooperation between rider and animal.

12. All of the hardware modules described can—and should—be provided with re-chargeable batteries in order to make them as simple as possible to operate.

13. a) All modules with re-chargeable batteries can be connected to charging units which charge the batteries, provided that the movement which can typically be expected can generate enough power to maintain continuous operation, or at least to extend the operating life per unit.

b) This charging movement per se can also result in the starting up of the module, or a cycle.

Ad 1. A GPS module connecting a GPS chip to a GSM chip, which transmits the location of the module together with the identifier at frequent intervals.

Ad 2. A girometer module which transmits the acceleration and/or position of the module by means of the connected GSM chip, in particular if carried on the user's body.

Example: The recognition of violent movements in order to prevent injuries and in order to identify and improve sequences of movement, for example in ballet or tennis.

Ad 3. A pulse sensor, whether incorporated in a pulse belt on the body, a wristband, or a smartwatch or implanted in the body, is connected to a GSM chip and transmits either the pulse or a simple (so called 1/3 point diagram) or comprehensive ECG (so called 6/7 point diagram) via the radio chip.

Ad 7. A connection can be made by means of the Bluetooth module from sensors or measuring devices which are not otherwise equipped with GSM for use in the described method.

Ad 8. a) WiFi module: standard

The same applies for a WiFi module in measuring devices which usually establish the connection to a normal transmitting device via WiFi and thereby use in the described method can occur.

Example: Stationary devices such as, for example, treadmills, the popular device in gyms today, which imitate climbing stairs, stationary rowing machines or so-called spinning wheels which imitate bicycles, frequently determine the relevant performance from the movement of the device, sometimes converted in a system of its own, and sometimes in an approximation of a distance covered as if the performance were produced outdoors. Sometimes further estimations are made using algorithms of the stationary device, thus—with the aid of bodyweight and size inputs—an estimation of the calories used during the training exercise. In order then to be able to connect these devices to the described system, the training sequence can be directly uploaded to the server via an integrated GSM chip or, since mostly stationary indoor sports equipment is involved, also via WLAN connection or other connection to the internet by means of a personal identifier which the user has to type in or which is registered in the WiFi module.

Here, users are free to transmit values from the pulse measuring device frequently incorporated in the equipment, or transmit his pulse data singly from his own pulse module and both pieces of information are combined on the server. If the device identifier and the figures ascertained there are now collectively transmitted via the WLAN to the server, or that data is sent from the user separately but at the same time, they can nevertheless be used together.

b) Chip-Reader Module

For the rare occasion on which an older module is involved, which stores data on a chip or an RFID card belonging to the user, an external device can be described in which the card is inserted and the data stored on it is transmitted to the server preferably along with the time and identifier. In this case, the algorithm for synchronising times described below will frequently not work. Thus it is up to the user to recognise the beginning of the sequence and to synchronise it subsequently using the other data transmitted.

Ad 9. By means of a switch module, i.e. a switch connected to a GSM chip, the user can build up or report a status depending on the status of the switch, so typically: 0=off, 1=on, or also 0, 1, 2, . . . depending on the click sequence or type of switch.

Example: Beginning and end of the training or training exercise; request to the trainer or a training algorithm.

Ad 10. A camera module can be used so that a user is monitored by a trainer during running sessions or other sports sessions and feedback given to the user via the server.

Enhancements

A) Hardware

1. Incorporating a Memory Chip for Interim or Permanent Storage

Memory chips can be incorporated in the modules for interim storage of data during a short-term failure of radio links and for sending it as a whole when the radio links are restored.

Memory chips can be incorporated in the same form in order to store data longer-term or permanently.

2. Cumulative Transmission of a Number of Measurements by a Device

In order to save power and to prevent permanent connection to the telephone network/internet, the intervals between measurement and transmission can be set so that they are different.

For Nordic walking for example it is sufficient for e.g. to locate a GPS signal every 15-90 seconds, but only to transmit this collected dataflow every 2-5 minutes.

3. Using One Measuring Device for a Number of People

The same measuring device can be used for different people, so other measuring modules can be switched off or set to a mode in which they use less energy.

In a walking group it is possible to detect with GPS modules that a number of people are walking at approximately the same pace and some GPS modules accordingly search for signals at longer intervals.

If at some point in time the signals differ, all modules can be set to a normal mode again.

4. Attaching an Additional WiFi Chip

In order to be able to save energy, above all during sports which frequently take place inside buildings such as gyms, a WLAN module can be added which switches off the GSM transmission where there is an authorised connection to the internet and instead transmits to the server by WLAN which frequently saves data tariffs and can occasionally be quicker.

5. Transfer of Data to Different Servers

Instead of data being sent to and stored on one server by the giving of an identifier and the assignment of the identifier to a measuring device, it is also possible to send to and store data on different servers (entry servers). The data can then be forwarded completely or in part to a calculation server for further processing, or a calculation server can then interrogate the entry server about the data received.

This saves, inter alia, processing time on the server and allows a fast transmission rate with less data traffic, since the measuring device's identifier is already indirectly held in the server which is being contacted.

B) Interaction Between Modules

In the method described, two or more modules can work together such that:

1. data transmitted to the server from at least two modules can be mutually processed in one algorithm, and/or 2. one algorithm uses one or a number of datasets from one or a number of measuring devices or sensors to make a calculation, and for meaningful further processing brings in further previously transmitted datasets in order to then process these further or just to connect them for information purposes, and/or 3. after the processing of one or a number of datasets from one or a number of modules, transmit information to a receiver module.

This is frequently only possible if time synchronisation occurs as described below.

Example: First, a case is described where the user carries on his person a GPS module, i.e. a GPS chip plus battery plus radio/GSM chip for transmitting the data. The module transmits the detected location to the server at pre-set intervals or even constantly. The user can subsequently view these values over the internet and can identify the timing, the locations using a superimposed map, or the speed which can be calculated back from the equation: distance between two fixed points divided by the time difference between the two points=speed. From this he can establish the point at which he began to run and where he stopped. This segment can then be defined as a training session.

If he now has this data available in the form of an interaction between the GPS module and pulse module, he can now also establish, from changes in his pulse, where he began the training sequence and where he finished it and can combine the captured data and thus obtain a more accurate picture of his training performance, the picture now being defined by the data on distance, speed and pulse rate.

Ad 3. a) In order to give the user simultaneous feedback:
the loudspeaker of a normal mobile phone—it does not have to be a smartphone in this case, it is enough to release the replay of the signal received,
the loudspeaker of a headphone module,
or some other specific loudspeaker module or a loudspeaker attached to a receiver device via radio link,
can be used to make information available to the user acoustically, this time the opposite way around, the information being sent from the server to the receiver device or receiver module and kept in the receiver module.

b) The same applies to visual feedback by means of a display on a smartwatch, a smartphone, an LCD or LED display or even other image representing devices.

c) aa) The headphone module described and the module for visual feedback can also be used in a modification of the invention in order to set up a connection between people by means of the server.

In this case, one described receiving device is sufficient as a loudspeaker or loudspeaker module on the part of the receiver. On the part of the transmitter, a microphone—with or without loudspeaker—must be attached, regardless of whether with or without loudspeaker.

In one modification a microphone can be connected on both sides.

bb) For visual feedback an input unit—a keyboard or touch display—must be incorporated on the transmitter side.

In one modification a keyboard or touch display can be connected on both sides.

Example: A trainer or judge can send instructions to a player or training partner via the server.

d) By means of the interposition of the server, it is possible to communicate with one another using simple mobile phones, which establish a connection to the mobile network. For this purpose, the receiver device is preferably called via a string to be transmitted.

e) In one modification of the invention a permanently transmitting microphone module can send tones to the server. Depending on the stored algorithm, if there is either a specific peak value ("doorbell"), a specific tone sequence ("baby crying") or a sustained tone ("baby phone"), this tone can be forwarded to a receiver unit consisting of at least one loudspeaker module, in particular to give the user an acoustic control of his household.

C) Combination Modules

In the following text the measuring devices xxx and yyy, which according to the method work together with both the battery and radio chip, always bear the name xxx, yyy module. Combination module is to be understood as the integration of at least two measuring devices into one module.

It is irrelevant whether a number of measuring devices each having a GSM chip are connected on the server, or whether a number of measuring devices having only one GPS chip in total are connected to a module.

There will frequently be combinations which make especially sense for a particular type of sport.

In order to avoid even small radio bridges, the measuring devices are frequently incorporated in larger and heavier measuring devices.

Example: The combination GPS and pulse sensor described below is ideal for running sports and cycling and other outdoor activities involving covering a distance. The positioning chip is preferably incorporated in the pulse belt.

In an enhancement of the invention two or more sensors which can be usefully combined with one another are thus connected with a GSM chip. In this case, alongside the module, chip or user identifier, the GSM chip also sends the two signals, whether successively in a string separated by an abbreviated identifier, or separately one after the other, or at the intervals in which the pieces of information arrive, possibly separately from one another.

1. Direct Connection Between the Measuring Devices in the Module

In a modification of the invention a measuring device is connected with another one such that one unit starts the other or alters its status, wherein the start or change sequence occurs directly between the two measuring devices. Alternatively, the sequence can be started or changed according to the described method by a signal from the server.

2. GPS-Pulse Module

It is irrelevant for the GPS-pulse module whether the measurement of the pulse and the positioning interval are the same or different.

A module with positioning and pulse is the perfect combination for running.

3. Camera-Switch Module

With a camera and a switch it can be ensured that the camera starts or that the continuously running camera immediately starts transmitting to the server, or retrospectively sends information which is temporarily stored in a memory after a specified time period. As well as switching the camera on, pressing the switch can also initiate another algorithm recognised in the server.

Example: Making contact with the trainer in order to get advice on how to do something better. A start-stop function for the tee-off in golf.

4. Camera-Girometer Module

The camera can be started and/or the transmission begun in a similar manner by means of the combination of camera and girometer, especially in the event of a fall. Here also it is not significant whether the start sequence occurs from girometer to camera or from girometer to server and the server starts the camera.

This combination is intended for particularly dangerous types of sports such as show jumping, for types of sports which require specific physical development such as judo or also golf, in which a follow-up inspection on safety grounds or in order to improve the user's technique is required particularly where there are quick movements or falls.

5. Camera-Light Sensor Module

The normal behaviour of the user can be monitored by means of camera-light sensor modules which control the recording.

Example: In hunting sports the behaviour of the hunter in the first moments of twilight; in day-to-day life, the opening of the fridge door with a camera/light sensor module installed inside; guarding bags from being robbed, for e.g. where luggage is handed over to airlines or in hotels; the camera is activated by being opened and the consequent inflow of light so that the face of the authorised or unauthorised opener can be immediately transmitted, thus opening the way to criminal proceedings.

C) Useful Algorithms

1. Synchronisation

In order to summarise the various sensor data assigned to one user the sensors need to be synchronised. Since the sensors do not communicate with one another, do not so-to-speak even know that there is another sensor, the server on which the information arrives must send an identifier to the same GSM chip at regular intervals and await a response, thus using the transmission time and the response time in order to detect a deviation by the sensor from the actual time. Since it knows both the receipt and the response times, the server can add or remove a time unit by calculation, in order to bring all of the sensors into synchronisation (the so-called doubled or "parallelogram synchronisation").

Example: If the GPS module is used together with the pulse module, the information can be made to overlap by means of the synchronisation algorithm mentioned so that a more accurate monitoring of the training exercise is carried out.

2. Pre-Setting of Sports Type According to the Location of the User

Since a user's sports types are frequently carried out in a specific location, such as running in a specific park area, cycling on a road, weight training, squash or spinning in a building, the positioning information, determined by GPS, can be taken, for sport types which are found in this area, to automatically originate from a specific sports type.

In the same way, by using the known type of movement, using accelerometer and/or girometer module values on a server, a sports type can be assigned by using the algorithm.

Thus if squash is offered at a gym and the girometer or accelerometer transmits a pattern of jumpy movements, the server can extrapolate a game pattern such as squash from that.

3. Algorithm for Speed Changes

Typically, in order to save energy, intervals between two positionings are generally set at one to two minutes.

The following algorithm can be applied regardless of whether there is a single transmission as described here or another detection by means of sports equipment such as a sports watch or even an application running on a smartphone or smartwatch.

The user can determine in advance that instead of a longer interval, if a particular determined speed is exceeded, the interval is reduced in order to make possible a better positioning and thus more accurate distance when making a difficult measurement.

Thus, where this speed is exceeded by 5-8 km/hr, it can be assumed that the user is running and, accordingly, a shorter interval can be selected. If he again exceeds a speed such as for example, typically 13-18 km/hr, another type of sport can be assumed, frequently cycling, and in some circumstances another interval, or the standard interval can be used. Where a further list speed is exceeded such as for example 50 km/hr, it can be assumed that the user is in a motorised device and again another interval or the standard interval can be used.

4. Change of Status by the Server

If the server can detect by means of a stored algorithm that there is a reason to change the status of a module, it can transmit this change request to the respective module and thus also to a sensor which could start in standby mode, or can prompt a module which is in standby mode, thus only ready-to-receive but not transmit, to re-set the status from "standby" to "active" ("Sleeping Beauty regulation").

Thus when, for example, an acceleration in the user's pulse is detected, the server can instruct other sensors to transmit more accurately, faster or to start transmitting. If the switch module described above is in operation, this can be connected with a stored sequence of status changes. The switch can be coded so that pressing twice could mean: I am beginning a running exercise with a correspondingly specific status for the user's different sensors stored in an algorithm. This transmission can take place independently of whether or not the user has the sensors and modules stored and assigned to him with him. At the same time, modules which would not be able to transmit any logical files can be switched off or into standby mode.

5 Comparison of Cell Data

In order to ensure that a number of modules are not delivering contradictory data, the cell identifier in which the user's modules are located can be compared. If there is a definitive performance attributed to the user, which is recorded on a module and sent to the server, the server can compare and determine, using GPS and/or a radio cell identifier, which sensors might have been carried by the user and which might not.

Example: If the user has a pair of training shoes in the car which she is currently driving, whilst the user is lifting weights in the gym a radio cell identifier of his pulse module and/or of the shoes he is currently wearing would report the proximity of the two modules to the server, whilst the training shoes in the car would not deliver any meaningful values and could thus be hidden or deleted.

6. Recognition of Movement Patterns

Since different sports types frequently have specific movement patterns, it can be detected, by means of a database which has been generally set up or maintained by the user, which movement pattern the transmitted girometer and/or accelerometer data should be attributed to. In this way, the corresponding sport can be stored and different sensors and the status of different sensor modules can be switched on and changed accordingly as described above.

7. Utilisation of Already Existing Sports Devices With Connections to a Smartphone/Smartwatch or Sports Watch For sports devices which frequently transmit data to the internet for retrospective overplay and evaluation via USB, Bluetooth or other wireless or wired connections, which is mostly provided by means of interposition of a smartphone or a smartwatch or a sports watch, this data can now be transmitted with the user's identifier to the server live and not necessarily processed via a program which is embedded in the end device and immediately processed there.

D) Specific Versions of Hardware for Specific Sports Types

1. Integrating Modules Into Balls

Up to now the assumption has always been that a sensor module is carried by the user. In sports types involving balls, in particular throwing sports (discus, ball, javelin and shot-put) as well as football, cricket, tennis, golf, the distance between the user and the ball frequently increases due to the characteristics of the sport type. With the proposed method, a module can now be inserted into the ball, for example a girometer module, and accelerometer module and/or a GPS module or a combination of at least two of these in order to also transmit the values for the ball or throwing device.

These values are not the values of the user, but are to be attributed to his sports type. Thus, where a GPS module is incorporated in a golf ball, for example in combination with a girometer, accelerometer, or vibration sensor module, it is possible to measure that a particular tee-off takes place at a specific time, how many meters were covered until the 1st, 2nd, 3rd . . . impact, and how far and where the ball subsequently rolls and where it comes to rest.

2. Incorporating Modules in Rackets/Bats/Clubs

Girometer modules can also be built into rackets/bats/clubs, in particular in tennis rackets, cricket bats and golf clubs, in order retrospectively to reproduce the movement and without taking pictures externally with a camera. This is of interest for pursuing haptic and motor-function training goals; thus in the golf swing it can be important whether the movement is made evenly in a round or an elliptical curve, this is currently done at great expense with external cameras at high speeds.

By combining this with the golf-ball module just described both movements can be summarised, i.e. the data ascertained from the movement of the golf club and the associated speed, distance and flight path of the ball.

a) The following are of interest for golfing sports:
a GPS module with a switch module in order to identify the beginning and end of the swing or the distance from the tee to the ball;
further, to build into the golf club an accelerometer module and the combination of GPS accelerometer module in the golf club as well as the incorporation in a golf ball of an accelerometer and/or a GPS module separately or combined.

In the described, simplest version GPS and switch module, the user can operate the switch at the tee-off, whereby the location just measured is transmitted (tee-off), and subsequently walk to the place where the ball has come to rest and there press the switch again (ball at rest), by which means the distance of the shot can be measured.

Where the accelerometer module is incorporated, the impact behaviour especially the power of the impact and the movement sequence can be illustrated. Where the GPS accelerometer module is incorporated, the accelerometer can be used to replace the above-mentioned switch. Thus each shot can be measured in the accelerometer, by the high speed with which it is associated, which can subsequently result in GPS tracking on a server from start to landing/rolling to a standstill.

This can also occur in a combination of a number of modules in different clubs, so that the same club does not need to be used, rather, the tracking always occurs when an impact can be detected by the accelerometer in the club or the ball.

b) Where a GPS is incorporated in a tennis racket the respective distance between 2 impacts can be measured whereby the user's performance during the game can be determined. If an accelerometer or a girometer is incorporated alongside the GPS, the power of the impact and the speed measurement can be made. As above, the speed of the ball following the impact can also be measured and transmitted by an accelerometer and/or GPS module incorporated in the rackets and the ball.

3. Inserting Modules Into Soles of Shoes a) After or already during the production of shoe soles, in particular those of sports shoes, modules can be incorporated, in particular GPS, girometer and accelerator modules or a combination of at least two of these three. This insertion means that the user can be sure that a training exercise and his daily walking will be recorded in any event, as long as all shoes have these modules available.

Thus he may already be engaged in sporting activity during the day and suddenly begin a running exercise without this having to be specially noted or potentially forgotten.

b) In an enhancement of the invention a rechargeable battery may be incorporated.

c) In an enhancement of the invention a rechargeable battery may be incorporated which is fed by a charging module which feeds itself from the movement of the user. If a module is used in a manner which involves vigorous movement, this movement can be used to charge the battery.

c) A start-stop function can also be incorporated by the movement module, whether by one of the built-in measuring devices or by the charging unit itself, i.e. by the baseline voltage created by sudden movement, since it can be assumed that a movement corresponds equally to a sporting or otherwise noteworthy movement.

d) The start-stop function can also be useful in principle in other modules, and added to them.

e) The charging function can also be useful in other modules as long as the expected movement can deliver enough energy for the safe use of the module in terms of the method described. By incorporating a re-chargeable battery the operating life of the module can be extended at the same time as enhancing its user friendliness; it may even be possible to do without external charging.

4. ODP Modules for Motor Sports and Use of Motor Driven Vehicles and Bicycles

A connection to motor driven vehicles can be made by an ODP module, especially for sports which are performed with such motor driven vehicles. An ideal combination in this case is an ODP module and an accelerometer.

Example: Racing cars or motorbikes: by means of a girometer and/or accelerometer module on a motorbike, it is possible to detect how the user is controlling the motorbike.

The same is true for connections to battery driven vehicles, mountain bikes and other such bicycles, whether connected by ODP or another interface.

5. Use of Drones with a GPS Module Carried on the User's Body

A user who wants to have his activity monitored continuously or periodically in order to check his running style can continuously transmit his location via a GPS module as described. This location can be used by a drone, also with GPS tracking, in order to direct its camera at the user from a distance of a few meters away from the user in order to record him and/or send the pictures to the server. The pictures can later be retrieved from the server or simultaneously sent to transmission devices—of the user or third parties—with visual playback. The drone can also, in the case of a fall, or following manual prompting, for e.g. by the switch module described, drop materials carried by it such as water or a first aid set.

EXAMPLES

There now follows an exemplary list of central aspects of the present invention. They principally serve to make an understanding of the present invention easier and should not be understood by the reader to be restrictive.

One aspect of the invention concerns a method, namely the de-coupling of measuring devices from a unitary receiver device and single transmission of the measured values by means of radio link, preferably mobile internet, telephone data link or other radio link in any frequency range, also via light, laser and infra-red, and transmissions in other frequencies, to a server—there to be stored, and simultaneously or subsequently processed together.

One aspect of the invention concerns a method, namely the simultaneous or subsequent transfer of all computing operations on one server.

One aspect of the invention concerns a method, namely the assignment to at least one user of the measured values and device identifiers, or otherwise the personal identification number including the transmission time, transmitted to a server.

One aspect of the invention concerns a method, namely the aggregation of the values assigned to a user within a specific time frame.

One aspect of the invention concerns a method, namely the carrying out of computing operations stored by algorithm on the server of the data transmitted as described above.

One aspect of the invention concerns a method, namely the return transmission of the information ascertained as described above to a receiver unit.

One aspect of the invention concerns a method, namely the attachment of the above module to an object or an animal in order to evaluate sporting or other day-to-day performances.

One aspect of the invention concerns a GPS module consisting of a GOS chip and a chip for radio transmission to a server preferably according to the above aspects of the invention.

One aspect of the invention concerns a girometer module consisting of a girometer chip and a chip for radio transmission to a server according to a method with the above aspects.

One aspect of the invention concerns a pulse module consisting of a pulse measuring device and a chip for radio transmission to a server according to a method with the above aspects.

One aspect of the invention concerns a SpO2 module consisting of a SpO2=blood-oxygen sensor and a chip for radio transmission to a server according to a method with the above aspects.

One aspect of the invention concerns a diabetes/CGM (constant glucose monitoring) module consisting of a diabetes measuring device and a chip for radio transmission to a server according to a method with the above aspects.

One aspect of the invention concerns a module with a sensor which measure useful values in at least approximate real time, and which values can describe directly or indirectly a state or change in state of a person, consisting of a sensor and a chip for radio transmission to a server according to a method with the above aspects.

One aspect of the invention concerns a module with another measuring device which measure useful values in at least approximate real time, and which values can describe directly or indirectly a state or change in state of a person, consisting of a sensor and a chip for radio transmission to a server according to a method with the above aspects.

One aspect of the invention concerns a Bluetooth module consisting of a Bluetooth receiver and a chip for radio transmission to a server according to a method with the above aspects, for connecting sensors and measuring devices provided with Bluetooth transmitters which are not originally intended for the method.

One aspect of the invention concerns a WiFi/WLAN module consisting of a WLAN receiver and a chip for radio transmission to a server according to a method with the above aspects for connecting sensors and measuring devices provided with WLAN which are not originally intended for the method.

One aspect of the invention concerns a WiFi/WLAN module consisting of a receiver and a chip for energy saving transmission to a server according to a method with the above aspects, particularly for devices in rooms with a WLAN connection.

One aspect of the invention concerns a switch module consisting of an electric-manual switch ("switch") and a chip for transmission to a server according to a method with the above aspects.

One aspect of the invention concerns a camera module consisting of a camera and a chip for transmission to a server according to a method with the above aspects.

One aspect of the invention concerns the installation of re-chargeable batteries in the modules described in the above aspects.

One aspect of the invention concerns charging units for the modules described above, which take energy from the movement of the module in order to power the chargeable batteries.

One aspect of the invention concerns a start-stop function for this movement.

One aspect of the invention concerns an incorporation of memory chips in the above-described modules in order to enable interim storage of data in the case of short-term failure of radio links, and to allow the data to be sent as a whole when the radio links are restored.

One aspect of the invention concerns an incorporation of memory chips in the above-described modules in order to enable longer-term storage of data.

One aspect of the invention concerns a setting of different intervals between measurement and transmission in the methods of the above aspects.

One aspect of the invention concerns using a measuring device as described above for different people and the short term switching off of other measuring devices or transferring them to a less energy-consuming state.

One aspect of the invention concerns an addition of a WiFi/WLAN chip to the above modules and a switching-off of the GSM transmission when there is an authorised connection to the internet via WLAN.

One aspect of the invention concerns a method as described above, but in which data is sent to different servers rather than just one.

One aspect of the invention concerns a method as described above, in which the data is forwarded completely or in part to a calculation server for further processing.

One aspect of the invention concerns a method as described above, in which the calculation server retrieves inputted data from the entry servers.

One aspect of the invention concerns a cooperation of two or more of the modules described above, in which data transmitted to the server by at least two modules is mutually processed in an algorithm.

One aspect of the invention concerns a cooperation of two or more of the modules described above, for calculation by means of an algorithm from one or a number of datasets of one or a number of measuring devices or sensors.

One aspect of the invention concerns a bringing in, as described above, of further already transmitted datasets in order to further process these or to merge them in an informative manner.

One aspect of the invention concerns a transmission of information to a receiver module after the processing of one or a number of datasets of one or a number of the modules described above.

One aspect of the invention concerns feedback to the user by means of a loudspeaker of a normal mobile phone, a headphones modules, or a loudspeaker incorporated in a smartphone, smartwatch, or of a specific loudspeaker module.

One aspect of the invention concerns feedback by means of radio link to a loudspeaker incorporated in a receiving device.

One aspect of the invention concerns a visual replay of the information described above by means of a display on the smartwatch, a smartphone, an LCD or LED display or even other image representing devices.

One aspect of the invention concerns the establishment of a connection between two people by means of the loudspeaker described above or by means of the module for visual replay described above.

One aspect of the invention concerns the connection of a microphone.

One aspect of the invention concerns the connection of a keyboard or touch display to a module as was described above.

One aspect of the invention concerns a communication between two mobile phones by means of interposition of the server according to the method described above.

One aspect of the invention concerns a microphone module which permanently transmits to the server, as was described above.

One aspect of the invention concerns the combination of at least two measuring devices and/or sensors according to the above description.

One aspect of the invention concerns a connection of one measuring device to another according to the combination mentioned above, in which one unit starts the other or changes its status, wherein the start or change sequence directly between the two measuring devices.

One aspect of the invention concerns a starting or changing of a sequence in a unit according to the combination mentioned above, by means of a signal from the server according to the method described.

One aspect of the invention concerns a connection of GPD chip with a pulse monitor according to the above description.

One aspect of the invention concerns a connection of a camera with a switch according to the above description.

One aspect of the invention concerns a combination of a camera and a girometer module according to the above description.

One aspect of the invention concerns a combination of a camera with a light-sensor module according to the above description, which controls the recording; thus the normal behaviour of the user can be monitored.

One aspect of the invention concerns a reconciliation of the timing data of different sensors measuring devices on the server according to the above description by means of synchronisation by the transmission of an identifier to a module and comparing the send-and-return time in order to calculate a deviation by the sensor from the actual time.

One aspect of the invention concerns the pre-setting of a sports type according to a known location according to the above description.

One aspect of the invention concerns the recognition of a sports type from the accelerometer and/or girometer module values on the server by the algorithm exploiting the known manner of movement according to the above description.

One aspect of the invention concerns a pre-setting in which instead of a longer interval being introduced when a particular determined speed is exceeded, the interval between two measurements is reduced in order to make possible a better positioning and thus more accurate distance when making a difficult measurement, regardless of whether this speed is detected according to the method described above or in another form.

One aspect of the invention concerns the transmission of a request to change the status of a module to the relevant module according to the above description.

One aspect of the invention concerns a comparison of the cell identifier the transmitting modules of a user in order to prevent contradictory data.

One aspect of the invention concerns a recognition, by means of a girometer and/or accelerometer, of movement patterns of different sports types using a database, which are carefully established/or determined in general or by the user, and accordingly as described above, the switching on and changing of the status of different sensor modules.

One aspect of the invention concerns a connection of sports devices which frequently transmit data to the internet for retrospective replay and evaluation via USB, Bluetooth or other wireless or wired connections, by means of transmitting the identifier to the server according to the method described above.

One aspect of the invention concerns an incorporation of measuring devices and sensor modules in balls according to the above description.

One aspect of the invention concerns an incorporation of measuring devices and sensor modules in rackets/bats/clubs according to the above description.

One aspect of the invention concerns an incorporation of measuring devices and sensor modules in the soles of shoes according to the above description.

One aspect of the invention concerns an incorporation of measuring devices and sensor modules in ODP modules according to the above description.

One aspect of the invention concerns an interaction of a GPS module with a drone equipped with a camera which obtains GPS data from the server and records the user from a certain distance.

The invention claimed is:

1. A sensor module for measuring body parameters, comprising:
   at least two sensors configured to respectively measure at least one parameter in order to generate corresponding sensor data; and
   a transmitter which is connected to the sensors, wherein the transmitter is configured to receive the sensor data from the sensor and send the sensor data directly to a remote server; and
   a memory chip configured to provide interim storage for the sensor data when there is a short-term failure in radio links and/or power supply and to send a whole of the sensor data when the radio links are restored, or to provide longer-term storage and send the sensor data in data packets;
   wherein one sensor is connected to the other sensor such that one sensor is configured to enable start of the other sensor or to alter status of the other sensor, wherein the start or alteration sequence occurs directly between the two sensors or wherein the start or alteration sequence is configured to be initiated by a signal from a remote server.

2. The sensor module according to claim 1, wherein the sensor module is incorporated in a sports device or sports equipment.

3. The sensor module according to claim 1, wherein the sensors are not capable of receiving or processing information from the remote server or any other source.

4. The sensor module according to claim 1, wherein the transmitter additionally sends a user identifier of a user to the remote server.

5. The sensor module according to claim 1, wherein the at least two sensors are selected from a group consisting of an ECG sensor, a blood pressure sensor, a blood sugar sensor, an SpO2 sensor, an acceleration sensor, a position sensor and a thermometer.

6. The sensor module according to claim 1, wherein the transmitter uses at least one mobile communications standard in order to transmit the sensor data to the remote server, wherein the mobile communications standard is selected from the group consisting of a public radio network standard, a regional mobile network standard, GSM, GPRS, Edge UMTS, HSDPA, HSPA+, LTE and LTE advanced.

7. The sensor module according to claim 1, wherein the transmitter is a one-way transmission system.

8. The sensor module according to claim 7, wherein the sensor module only transmits information and not to receive queries or instructions.

9. The sensor module according to claim 1, wherein the transmitter uses at least one short-range radio frequency and wherein the short-range radio frequency corresponds to a communications standard selected from the group consisting of Bluetooth, IEEE 802.11 and IEEE 802.11 a, ac, ad, b, g, h or n.

10. The sensor module according to claim 1, further comprising:
    a battery which supplies energy to the transmitter and the sensors; and
    a memory which stores the sensor data in case the battery power has become too weak to supply the transmitter with enough energy.

11. The sensor module according to claim 1, wherein measurement data transmitted to the server further comprises a device identifier, personal identifier and/or time identifier for at least one user.

12. An evaluation system for a sensor module comprising:
    a sensor module according to claim 1;
    a remote server which receives the sensor data from the transmitter; wherein measurement data of a user transmitted to the server is summarised and/or evaluated in the server within a specific timeframe.

13. The evaluation system according to claim 12, wherein timing data from different sensors and measuring devices is reconciled on the server by means of synchronisation by sending an identifier to a module and comparing the send-and-return time in order to determine a deviation by the sensor from the actual time.

14. The evaluation system according to claim 12, wherein the remote server directly stores and/or evaluates the information received from the sensor module.

15. The evaluation system according to claim 12, wherein the server sends instructions to a mobile device of the user which, by means of an algorithm stored on the server, were calculated from at least one variable characteristic of the sensor module.

\* \* \* \* \*